(12) United States Patent
Sohn et al.

(10) Patent No.: US 12,234,310 B2
(45) Date of Patent: Feb. 25, 2025

(54) BLOOD-COMPATIBLE FLUORINE-BASED POLYMER AND THIN FILM COMPRISING SAME

(71) Applicant: KOREA RESEARCH INSTITUTE OF CHEMICAL TECHNOLOGY, Daejeon (KR)

(72) Inventors: Eun Ho Sohn, Daejeon (KR); Dong Je Han, Daejeon (KR); Hyeon Jun Heo, Daejeon (KR); Jeong Kim, Daejeon (KR); In Joon Park, Daejeon (KR); Jong Wook Ha, Daejeon (KR); Soo Bok Lee, Daejeon (KR); Hong Suk Kang, Daejeon (KR); Sang Goo Lee, Daejeon (KR); Shin Hong Yook, Daejeon (KR)

(73) Assignee: KOREA RESEARCH INSTITUTE OF CHEMICAL TECHNOLOG, Daejeon (KR)

( * ) Notice: Subject to any disclaimer, the term of this patent is extended or adjusted under 35 U.S.C. 154(b) by 799 days.

(21) Appl. No.: 17/351,924

(22) Filed: Jun. 18, 2021

(65) Prior Publication Data
US 2021/0395424 A1 Dec. 23, 2021

Related U.S. Application Data

(63) Continuation-in-part of application No. PCT/KR2019/017415, filed on Dec. 10, 2019.

(30) Foreign Application Priority Data

Dec. 20, 2018 (KR) .................. 10-2018-0166493

(51) Int. Cl.
*C08F 259/08* (2006.01)
*A61L 31/10* (2006.01)
(Continued)

(52) U.S. Cl.
CPC ............ *C08F 259/08* (2013.01); *A61L 31/10* (2013.01); *C08J 5/18* (2013.01); *C08L 27/24* (2013.01);
(Continued)

(58) Field of Classification Search
CPC . C08F 259/08; A61L 31/10; C08J 5/18; C08J 2327/24; C08L 27/24; C09D 127/24
See application file for complete search history.

(56) References Cited

U.S. PATENT DOCUMENTS

| 5,282,854 A | 2/1994 | Yagi et al. |
| 2004/0063805 A1 | 4/2004 | Pacetti et al. |
| 2007/0244262 A1 | 10/2007 | Zhang et al. |

FOREIGN PATENT DOCUMENTS

| JP | 09067417 A | 3/1997 |
| JP | 2013177494 A | 9/2013 |

OTHER PUBLICATIONS

PCT International Search Report dated Mar. 17, 2020 for International Application No. PCT/KR2019/017415, from which the instant application is based, 5 pages.

*Primary Examiner* — Ling Siu Choi
*Assistant Examiner* — Andrea Wu
(74) *Attorney, Agent, or Firm* — Fredrikson & Byron, P.A.

(57) ABSTRACT

Disclosed is a blood-compatible polymer represented by Formula 1. A polymer obtained by grafting a fluorinated methacrylate onto a polyvinylidene fluoride copolymer and provided in one aspect of the present invention is a polymer with blood compatibility, and may provide a blood-compatible material with hydrophobicity. In addition, it is possible to provide a material with controlled contact angle and surface energy properties by controlling the hydrogen fluoride length of the fluorinated methacrylate monomer for modification. Furthermore, it is possible to provide coating (Continued)

with controlled surface properties and blood compatibility through a simple process. Furthermore, it is possible to provide a freestanding polymer film with blood compatibility.

10 Claims, 7 Drawing Sheets

(51) Int. Cl.
    *C08J 5/18*          (2006.01)
    *C08L 27/24*        (2006.01)
    *C09D 127/24*      (2006.01)
(52) U.S. Cl.
    CPC ......... *C09D 127/24* (2013.01); *C08J 2327/24* (2013.01)

P(VDF-CTFE)-g-TFEMA
example 7

P(VDF-CTFE)-g-PFPMA
example 8

P(VDF-CTFE)-g-TFEMA
example 9

Fig.7
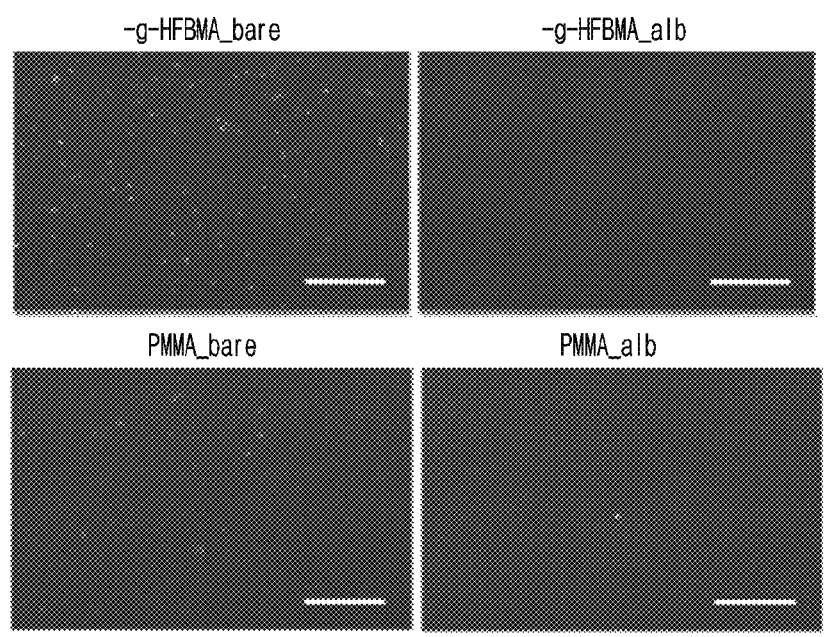
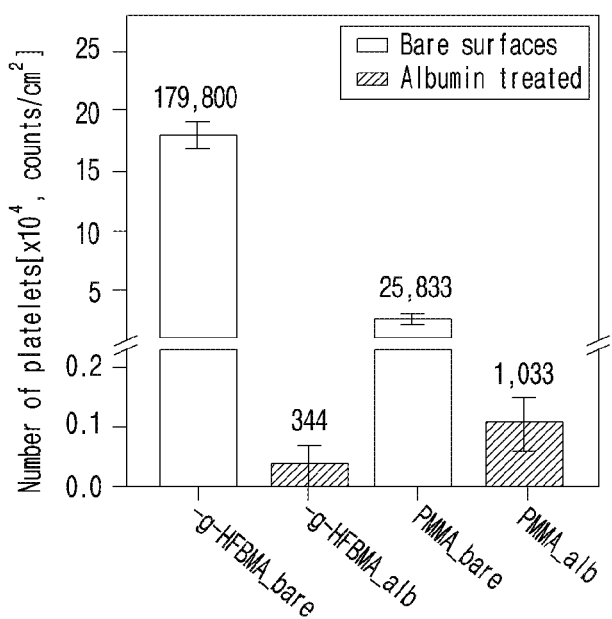

BLOOD-COMPATIBLE FLUORINE-BASED POLYMER AND THIN FILM COMPRISING SAME

TECHNICAL FIELD

The present disclosure relates a blood-compatible fluorine-based polymer and a thin film including the same.

BACKGROUND ART

With the aging of the population, the number of patients with acute and chronic cardiopulmonary dysfunction disorders or circulatory system disorders is increasing. In order to deal with such disorders, the number of a surgical operation performed for circulating blood outside a body, such as in vitro cardiopulmonary bypass, cardiopulmonary bypass, dialysis, and the like, is rapidly increasing. Therefore, the global demand for equipment and materials used in these in vitro circulators continues to increase.

Despite the increase in usage and demand, it has been reported that, in the case of an in vitro oxidizer procedure applied to patients suffering from cardiopulmonary failure, the survival rate when the procedure is performed is not much different when compared to the survival rate before the procedure is performed. Therefore, it is time for efforts in the medical community to increase the survival rate when using equipment as well as research to improve equipment.

Particularly, research on materials directly contacting blood is important. This is because when blood comes into contact with equipment, various protein adsorption occurs on the surface, and as a result, there are side effects such as blood clotting or an immune action, which may put a patient's at risk. In order to prevent the side effects, the blood compatibility of a material becomes a major issue.

In order to find out the degree of blood compatibility, the adsorption amount of a protein is typically measured. Among proteins, protein albumin is a protein which occupies the largest amount of blood, but is known not to significantly affect blood compatibility. Fibrinogen is a factor directly related to a blood clotting chain reaction, and is known to be able to clot whole blood even with an adsorption amount of only 10 nanograms per square centimeter.

A well-known blood-compatible polymer is polyethylene glycol (poly(ethylene glycol)), which is a hydrophilic polymer, and the polyethylene glycol retains water molecules on the surface thereof, and thus, prevents the adsorption of proteins. However, the polyethylene glycol is decomposed in water and has a limitation due to a wetting phenomenon. Therefore, there has been the need for a hydrophobic polymer which may be stably present in water for a longer period of time, and which is not subjected to wetting or swelling.

An organic fluorine polymer material exhibits unique properties, such as low energy surface properties, heat resistance, stability, and chemical resistance, which are different from those of other polymer materials. In addition, the organic fluorine polymer material has hydrophobicity as well as controlled surface properties obtained by controlling the number of fluorinated carbons, and thus, has sufficient potential to be used as a blood-compatible material.

DISCLOSURE OF THE INVENTION

Technical Problem

Accordingly, while conducting research on a hydrophobic blood-compatible material and the properties thereof, the present inventors synthesized a graft polymer of a polyvinylidene fluoride copolymer by modification using a fluorine-based methacrylate, and confirmed that the polymer may be made into a thin film to be used as a blood-compatible material, and completed the present invention.

One object of the present invention is to provide a hydrophobic blood-compatible polymer, a composition including the same, and a method for preparing the same in order to solve the long-term stability problem, a wetting phenomenon, and a swelling phenomenon of an existing hydrophilic blood-compatible material, wherein the hydrophobic blood-compatible polymer may be applied to a medical device which comes into contact with blood.

Another object of the present invention is to provide a blood-compatible thin film formed by coating a composition including the blood-compatible polymer.

Still another object of the present invention is to provide a freestanding polymer film including the blood-compatible polymer.

Technical Solution

In order to achieve the objects, the present invention provides a blood-compatible polymer represented by Formula 1 below.

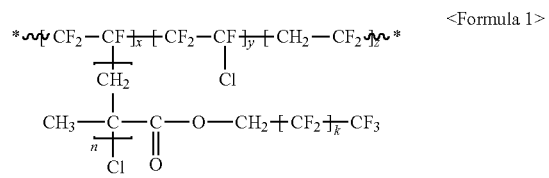

<Formula 1>

(In Formula 1 above, x is a mole fraction and is a real number satisfying 0<x<1, y is a mole fraction and is a real number satisfying 0<y<1, z is a mole fraction and is a real number satisfying 0<z<1, wherein x+y+z=1, n is an integer of 5 to 200, and k is an integer of 0 to 6.)

The present invention also provides a method for preparing a blood-compatible polymer, the method including mixing a metal catalyst, a ligand, a solvent, and a fluorinated methacrylate monomer by using a copolymer (P(VDF-CTFE)) of vinylidene fluoride (VDF) and chlorotrifluoroethylene (CTFE) as a macro initiator to prepare a mixed solution.

Furthermore, the present invention provides a blood-compatible polymer composition including a blood-compatible polymer represented by Formula 1 above and a solvent.

The present invention also provides a method for preparing a hydrophobic thin film, the method including dissolving the polymer in a solvent to prepare a mixed solution, and coating the mixed solution.

Furthermore, the present invention provides a freestanding polymer film including a blood-compatible polymer represented by Formula 1 above.

Advantageous Effects

A polymer obtained by grafting a fluorinated methacrylate onto a polyvinylidene fluoride copolymer and provided in one aspect of the present invention is a polymer with blood compatibility, and may provide a blood-compatible material with hydrophobicity. In addition, it is possible to provide a material with controlled contact angle and surface energy properties by controlling the hydrogen fluoride length of the fluorinated methacrylate monomer for modification. Furthermore, it is possible to provide coating with controlled surface properties and blood compatibility through a simple process. Furthermore, it is possible to provide a freestanding polymer film with blood compatibility.

BRIEF DESCRIPTION OF THE DRAWINGS

FIG. 7 is a SEM photograph of platelets attached to the surface of each of bare P(VDF-CTFE)-g-HFBMA (-g-HFBMA_bare), albumin-treated (PVDF-CTFE)-g-HFBMA (-g-HFBMA_alb), bare PMMA (PMMA_bare), and albumin-treated PMMA (PMMA_alb), and a graph showing the number of platelets on the surface calculated.

BEST MODE FOR CARRYING OUT THE INVENTION

Figure 1:
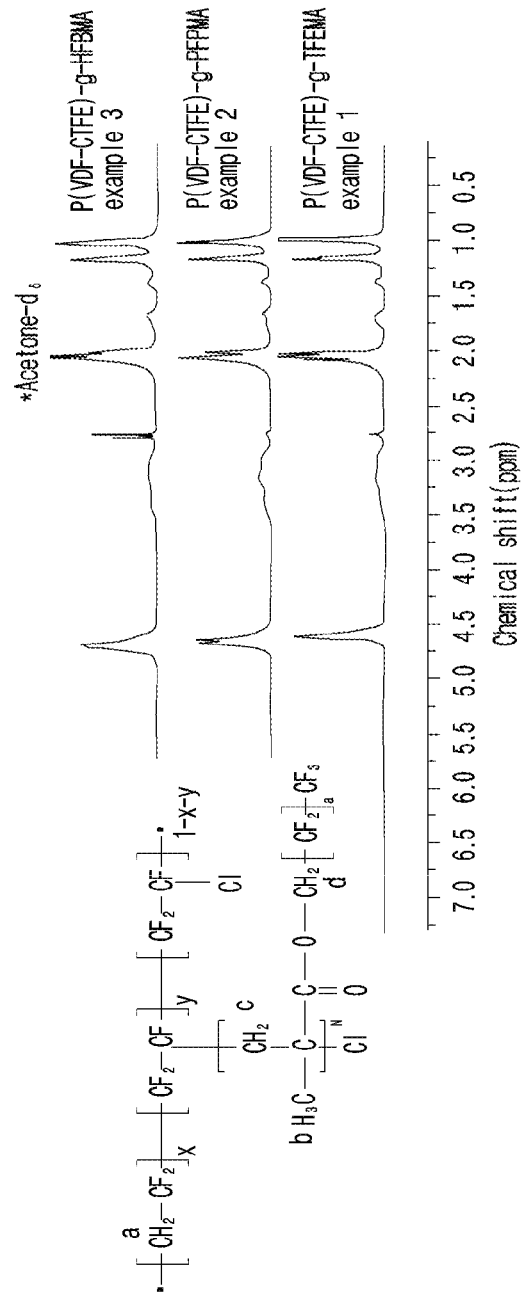
FIG. 1 is a graph showing the result of analyzing a blood-compatible graph polymer prepared in each of Examples 1 to 3 by nuclear magnetic resonance spectrometry (NMR)

According to an aspect of the present invention, there is provided a blood-compatible polymer represented by Formula 1 below.

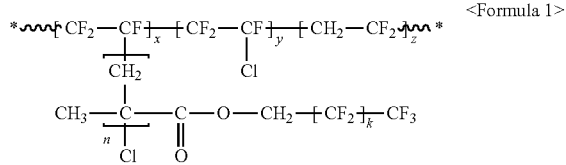

<Formula 1>

(In Formula 1 above, x is a mole fraction and is a real number satisfying 0<x<1, y is a mole fraction and is a real number satisfying 0<y<1, z is a mole fraction and is a real number satisfying 0<z<1, wherein x+y+z=1, n is an integer of 5 to 200, and k is an integer of 0 to 6.)

Hereinafter, the blood-compatible polymer provided in one aspect of the present invention will be described in detail.

A polymer provided in one aspect of the present invention is a polymer in which fluorine-based methacrylate is modified and grafted onto a copolymer of vinylidene fluoride (VDF) and chlorotrifluoroethylene (CTFE), and exhibits blood-compatible properties. The polymer is a polymer which may be applied as a blood-compatible material, and may exhibit blood compatibility not causing various protein adsorption when comes into direct contact with blood.

The blood-compatible polymer is represented by Formula 1, and k may be 0 or greater, 0 to 6, 0 to 3, or 0 to 2. In addition, the k may be 1 or greater, 1 to 3, or 1 to 2. Furthermore, the k may be 2 or greater, or 2 to 3.

According to another aspect of the present invention, there is provided a method for preparing a blood-compatible polymer, the method including mixing a metal catalyst, a ligand, a solvent, and a fluorinated methacrylate monomer by using a copolymer (P(VDF-CTFE)) of vinylidene fluoride (VDF) and chlorotrifluoroethylene (CTFE) as a macro initiator to prepare a mixed solution.

Hereinafter, the method for preparing a blood-compatible polymer provided in another aspect of the present invention will be described in detail.

The method for preparing a blood-compatible polymer provided in another aspect of the present invention includes mixing a metal catalyst, a ligand, a solvent, and a fluorinated methacrylate monomer by using a copolymer (P(VDF-CTFE)) of vinylidene fluoride (VDF) and chlorotrifluoroethylene (CTFE) as a macro initiator to prepare a mixed solution.

At this time, the fluorinated methacrylate monomer includes —(CF)$_k$—CF$_3$, and k may be 0 or greater, 0 to 6, 0 to 3, or 0 to 2. In addition, the k may be 1 or greater, 1 to 3, or 1 to 2. Furthermore, the k may be 2 or greater, or 2 to 3. When the k exceeds 6, there is a problem in that solubility with respect to a solvent decreases and accumulation in body occurs, and when the k is 0, there is a problem in that blood compatibility decreases.

In addition, as the fluorinated methacrylate monomer, one or more among trifluoroethyl methacrylate (TFEMA), pentafluoropropyl methacrylate (PFPMA), heptafluorobutyl methacrylate (HFBMA), and nonafluorohexyl methacrylate (NFHMA) may be used alone, or in combination.

Furthermore, the solvent may be used without any particular limitation as long as it is a typical solvent capable of dissolving P(VDF-CTFE) which is used as a macro initiator. However, it is preferable to use N-methyl 2-pyrrolidone, dimethylformamide, dimethylsulfoxide, and the like alone or in combination, more preferably, N-methyl 2-pyrrolidone.

In addition, the metal catalyst may be a monovalent copper metal catalyst. For example, a monovalent copper chloride or a monovalent copper bromide may be used, and it is more preferable to use a monovalent copper chloride.

Furthermore, as the ligand, 2,2-bipyridine, pentamethyldiethylenetriamine, 4,4-dimethyldipyridyl, and the like, which may form a mixed body with metal ions which are applied as a metal catalyst and included, may be used. However, it is preferable to use 2,2-bipyridine.

In addition, the concentration of the macro initiator in the mixed solution may be 0.01 g/ml to 0.05 g/ml, or 0.02 g/ml to 0.035 g/ml.

Furthermore, the concentration of the fluorinated methacrylate monomer in the mixed solution may be 0.1 g/ml to 0.5 g/ml, or 0.1 g/ml to 0.3 g/ml.

In addition, the concentration of the metal catalyst in the mixed solution may be 0.001 g/ml to 0.01 g/ml, or 0.003 g/ml to 0.007 g/ml.

Furthermore, the concentration of the ligand in the mixed solution may be 0.005 g/ml to 0.03 g/ml, or 0.001 g/ml to 0.02 g/ml.

In addition, the method for preparing a blood-compatible polymer provided in another aspect of the present invention may include polymerizing the mixed solution.

The polymerization may be performed in an inert gas atmosphere, and as a specific example, may be performed in a nitrogen gas atmosphere.

In addition, the polymerization may be performed at a temperature of 70° C. to 110° C., or at a temperature of 80° C. to 100° C. Furthermore, the polymerization may be performed at a stirring speed of 300 rpm to 900 rpm.

The mixed solution prepared in the above preferred ranges was subjected to polymerization at a temperature of 90° C. and a stirring speed of 300 to 900 rpm under nitrogen atmosphere, and as a result, fluorinated methacrylate was grafted onto a copolymer of vinylidene fluoride and chlorotrifluoroethylene to provide a polymer wherein the surface properties thereof may be controlled.

Furthermore, in another aspect of the present invention, there is provided a blood-compatible polymer composition including a blood-compatible polymer represented by Formula 1 above and a solvent.

The composition provided in another aspect of the present invention is a mixture of a polymer in which fluorine-based methacrylate is modified and grafted onto a copolymer of vinylidene fluoride (VDF) and chlorotrifluoroethylene (CTFE) and a solvent, and exhibits blood-compatible properties. The polymer is a polymer which may be applied as a blood-compatible material, and may exhibit blood compatibility not causing various protein adsorption when comes into direct contact with blood.

The blood-compatible polymer is represented by Formula 1, and k may be 0 or greater, 0 to 6, 0 to 3, or 0 to 2. In addition, the k may be 1 or greater, 1 to 3, or 1 to 2. Furthermore, the k may be 2 or greater, or 2 to 3.

In addition, the solvent may be used without a limitation as long as it is a solvent capable of dissolving the blood-compatible polymer, and as a specific example, trifluorotoluene, acetone, ethylmethylketone, tetrahydrofuran, dimethylformamide, chloroform, N-methyl-2-pyrrolidone (NMP), and the like may be used alone or in combination. However, it is preferable to use tetrahydrofuran which has good solubility and is rapidly volatilized.

Furthermore, in the composition, the content of the blood-compatible polymer is not particularly limited, but is preferably 0.5 wt % to 15 wt %, 0.5 wt % to 10 wt %, or 1 wt % to 5 wt % considering solubility, coating using the composition, or formation of a stable thin film.

In addition, the composition may be applied to a device such as a blood container, in vitro blood circulation equipment, and body transplant medical equipment.

Furthermore, in yet another aspect of the present invention, there is provided a method for preparing a hydrophobic thin film, the method including dissolving the polymer in a solvent to prepare a mixed solution, and coating the mixed solution.

Hereinafter, each step of the method for preparing a hydrophobic thin film provided in yet another aspect of the present invention will be described in detail.

First, the method for preparing a hydrophobic thin film provided in yet another aspect of the present invention includes dissolving the polymer in a solvent to prepare a mixed solution.

At this time, the solvent is provided in one aspect of the present invention, and may be used without any particular limitation as long as it is a typical solvent capable of dissolving a blood-compatible polymer. As a specific example, it is preferable to use trifluorotoluene, acetone, ethylmethylketone, tetrahydrofuran, dimethylformamide, chloroform, N-methyl-2-pyrrolidone (NMP), and the like alone or in combination, and it is more preferable to use trifluorotoluene.

In addition, the content of a polymer in the mixed solution is not particularly limited as long as it is a concentration at which coating or supporting may be performed, but is preferably 0.5 wt % to 15 wt %, more preferably 0.5 wt % to 10 wt %, or 0.5 wt % to 3 wt % in order to form a stable thin film surface.

Next, the method for preparing a hydrophobic thin film provided in yet another aspect of the present invention includes coating the mixed solution.

At this time, the coating may be performed on the surface of a base material, and the base material may be used without any particular limitation as long as it is a material capable of coating a hydrophobic thin film. However, it is preferable to use paper, fiber, filter, patterned surface, glass, metal, plastic, ceramic, and the like, and it is preferable to use metal, glass, plastic surface, and the like.

In addition, the coating may be performed by any method without a particular limitation as long as it is a method capable of coating a hydrophobic thin film on a base material. However, spin coating, dip coating, roll coating, solution coating, spray coating, and the like are preferable.

The method for preparing a hydrophobic thin film provided in another aspect of the present invention may allow a hydrophobic thin film to be easily and simply formed. In addition, through a protein adsorption experiment for evaluating blood compatibility, it was confirmed that the thin film had blood compatibility. Therefore, the thin film may be usefully used as a hydrophobic thin film capable of contacting blood.

Furthermore, in another aspect of the present invention, there is provided a freestanding polymer film including a blood-compatible polymer represented by Formula 1 above.

Figure 5:
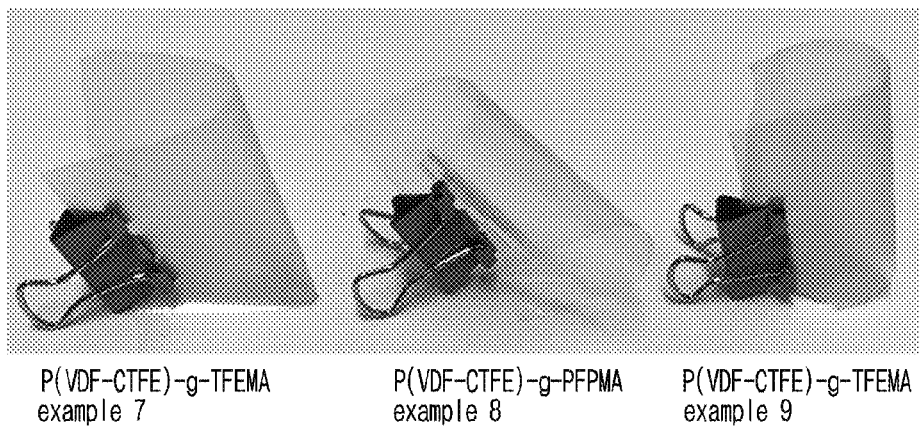
FIG. 5 is a photograph of a freestanding polymer film prepared in each of Example 7 to Example 9.

The freestanding polymer film provided in another aspect of the present invention is a freestanding hydrophobic polymer film formed by being dried on a base material, such as a substrate, and FIG. 5 shows a photograph of the freestanding polymer film.

A homopolymer of fluorine methacrylate is poor in physical properties, and thus, coating is possible, but a freestanding polymer film is not prepared. However, when a blood-compatible polymer having the structure represented by Formula 1 above is used, a free-standing polymer film with controlled surface properties and blood compatibility is prepared, so that it is possible to prepare a polymer composition in a form easier to be actually applied than a polymer coated only in a thin film form.

The polymer film may be applied to a device such as a blood container, in vitro blood circulation equipment, and body transplant medical equipment.

MODE FOR CARRYING OUT THE INVENTION

Hereinafter, the present invention will be described in detail with reference Examples and Experimental Examples.

However, the following Examples and Experimental examples are only illustrative of the present invention, and the scope of the present invention is not limited by the Examples and Experimental Examples.

<Example 1> Preparation of Polyvinylidene Fluoride-Based Blood-Compatible Polymer 1

1 g of a copolymer (PVDF-CTFE, VDF:CTFE=73:27 mol %) of vinylidene fluoride (VDF) and chlorotrifluoroethylene (CTFE), 30 ml of N-methylpyrrolidone, 0.15 g of copper chloride (I), 6 g of trifluoroethyl methacrylate (TFEMA), and 0.3 g of 2,2-bipyridine were added in a 100 ml reaction vessel, and reacted at a reaction temperature of 90° C. and a stirring speed of 400 rpm in a nitrogen environment to prepare a graft copolymer (P(VDF-CTFE)-g-TFEMA) in which trifluoroethyl methacrylate (TFEMA), which is a fluorinated methacrylate having one fluorocarbon, is grafted onto a copolymer of vinylidene fluoride and trifluoroethylene.

<Example 2> Preparation of Polyvinylidene Fluoride-Based Blood-Compatible Polymer 2

1 g of a copolymer (PVDF-CTFE, VDF:CTFE=73:27 mol %) of vinylidene fluoride (VDF) and chlorotrifluoroethylene (CTFE), 30 ml of N-methylpyrrolidone, 0.15 g of copper chloride (I), 7.7 g of pentafluoropropyl methacrylate (PFPMA), and 0.3 g of 2,2-bipyridine were added in a 100 ml reaction vessel, and reacted at a reaction temperature of 90° C. and a stirring speed of 400 rpm in a nitrogen environment to prepare a graft copolymer (P(VDF-CTFE)-g-PFPMA) in which pentafluoropropyl methacrylate (PFPMA), which is a fluorinated methacrylate having two fluorocarbons, is grafted onto a copolymer of vinylidene fluoride and trifluoroethylene.

<Example 3> Preparation of Polyvinylidene Fluoride-Based Blood-Compatible Polymer 3

1 g of a copolymer (PVDF-CTFE, VDF:CTFE=73:27 mol %) of vinylidene fluoride (VDF) and chlorotrifluoroethylene (CTFE), 30 ml of N-methylpyrrolidone, 0.15 g of copper chloride (I), 9.5 g of heptafluorobutyl methacrylate (HFBMA), and 0.3 g of 2,2-bipyridine were added in a 100 ml reaction vessel, and reacted at a reaction temperature of 90° C. and a stirring speed of 400 rpm in a nitrogen environment to prepare a graft copolymer (P(VDF-CTFE)-g-HFBMA) in which heptafluorobutyl methacrylate (HFBMA), which is a fluorinated methacrylate having three fluorocarbons, is grafted onto a copolymer of vinylidene fluoride and trifluoroethylene.

<Example 4> Preparation of Hydrophobic Thin Film with Blood Compatibility 1

The graft copolymer (Example 1) in which trifluoroethyl methacrylate (TFEMA), which is a fluorinated methacrylate having one fluorocarbon, is grafted onto a copolymer of vinylidene fluoride and trifluoroethylene was dissolved in a trifluorotoluene solvent at room temperature to prepare a polymer solution with a 1 wt % concentration.

Next, the polymer solution was spin coated at a rotational speed of 3000 rpm for 60 seconds and dried to prepare a hydrophobic thin film.

<Example 5> Preparation of Hydrophobic Thin Film with Blood Compatibility 2

The graft copolymer (Example 2) in which pentafluoropropyl methacrylate (PFPMA), which is a fluorinated methacrylate having two fluorocarbons, is grafted onto a copolymer of vinylidene fluoride and trifluoroethylene was dissolved in a trifluorotoluene solvent at room temperature to prepare a polymer solution with a 1 wt % concentration.

Next, the polymer solution was spin coated at a rotational speed of 3000 rpm for 60 seconds and dried to prepare a hydrophobic thin film.

<Example 6> Preparation of Hydrophobic Thin Film with Blood Compatibility 3

The graft copolymer (Example 3) in which heptafluorobutyl methacrylate (HFBMA), which is a fluorinated methacrylate having three fluorocarbons, is grafted onto a copolymer of vinylidene fluoride and trifluoroethylene was dissolved in a trifluorotoluene solvent at room temperature to prepare a polymer solution with a 1 wt % concentration.

Next, the polymer solution was spin coated at a rotational speed of 3000 rpm for 60 seconds and dried to prepare a hydrophobic thin film.

<Example 7> Preparation of Freestanding Polymer Film with Blood Compatibility 1

The graft polymer prepared in Example 1 and grafted with trifluoroethyl methacrylate (TFEMA) was dissolved in a tetrahydrofuran solvent under the temperature condition of 60° C. to prepare a polymer solution with a 7 wt % concentration.

Next, the solution was dried on a glass substrate to prepare a freestanding polymer film.

<Example 8> Preparation of Freestanding Polymer Film with Blood Compatibility 2

The graft polymer prepared in Example 2 and grafted with pentafluoropropyl methacrylate (PFPMA) was dissolved in a tetrahydrofuran solvent under the temperature condition of 60° C. to prepare a polymer solution with a 7 wt % concentration.

Next, the solution was dried on a glass substrate to prepare a freestanding polymer film.

<Example 9> Preparation of Freestanding Polymer Film with Blood Compatibility 3

The graft polymer prepared in Example 3 and grafted with heptafluorobutyl methacrylate (HFBMA) was dissolved in a tetrahydrofuran solvent under the temperature condition of 60° C. to prepare a polymer solution with a 7 wt % concentration.

Next, the solution was dried on a glass substrate to prepare a freestanding polymer film.

<Comparative Example 1> Preparation of Hydrophobic Thin Film with Blood Compatibility A polymer solution of a 1 wt % concentration was prepared by dissolving, instead of a graft copolymer based on polyvinylidene fluoride, a polymethyl methacrylate (PMMA) polymer (weight average molecular weight=12000), which is a universal polymer also used as a medical polymer, in a trifluorotoluene solvent at room temperature.

Next, the polymer solution was spin coated at a rotational speed of 3000 rpm for 60 seconds and dried to prepare a hydrophobic thin film.

<Experimental Example 1> Composition Analysis and Contact Angle Evaluation of Hydrophobic Thin Film Including Polymer According to the Present Invention 1. Composition Analysis In order to analyze the composition of a blood-compatible polymer material according to the present invention and a hydrophobic thin film containing the same, the polymers prepared in Examples 1 to 3 were analyzed using nuclear magnetic resonance spectrometry (1H-NMR, Bruker AVANCE 500), and the results are shown in FIG. 1.

2. Contact Angle Evaluation

In order to evaluate the contact angle between the blood-compatible polymer material according to the present invention and the hydrophobic thin film containing the same, 3 μl of water droplets and diiodomethane were dropped on the surface of the hydrophobic thin films on a silicon wafer prepared in Examples 4 to 6 above. A contact angle during a 1-minute additional injection of 10 μl of water was recorded to measure a contact angle by a dynamic contact angle measurement method. The present experiment was conducted using Kruss DSA100 (Germany) contact angle measurement equipment, and the results are shown in Table 1 below.

TABLE 1

| Classification | Water contact angle (°) | Diiodomethane contact angle (°) |
| --- | --- | --- |
| Example 4 | 101.4 | 79.2 |
| Example 5 | 110.7 | 90.7 |
| Example 6 | 114.8 | 94.4 |

As shown in FIG. 1, it was confirmed that the graft copolymers prepared in Examples 1 to 3 exhibited the characteristic peak of both a hydrogen adjacent to polyvinylidene fluoride and a hydrogen in fluorinated methacrylate.

Table 1 above shows that a hydrophobic thin film was formed according to the present invention. In particular, in the case of Example 6, the water contact angle shows a value similar to that of a Teflon resin (PTFE).

In addition, it can be confirmed that surface properties change when the number of fluorocarbons of the fluorinated methacrylate, which is a grafted monomer, increases (when changing from Example 4 to Example 6).

Furthermore, it was shown that the greater the number of fluorocarbons in the monomer, the greater the contact angle with respect to water and also diiodomethane, which is an organic solvent.

Therefore, it was found that different types of fluorinated methacrylate were successfully grafted onto a copolymer of vinylidene fluoride and trifluoroethylene by the present invention, and it was found that the surface properties of a hydrophobic thin film were controlled, accordingly.

<Experimental Example 2> Analysis of Blood Compatibility of Hydrophobic Thin Film Through Protein Adsorption Experiment A protein adsorption experiment was conducted to analyze the basic blood compatibility of the hydrophobic thin films of Examples 4 to 6 and the thin film of Comparative Example 1 according to the present invention. Albumin and fibrinogen were made into solutions of 5 mg/ml and 0.3 mg/ml respectively, and used as two model proteins for the analysis, and an adsorption amount was measured by using a quartz crystal electronic microbalance (QCM, biotin scientific E1) under the conditions of 37° C. and a flow of 0.1 ml per minute, and the results are shown in FIGS. 2 to 4.

Figure 2:
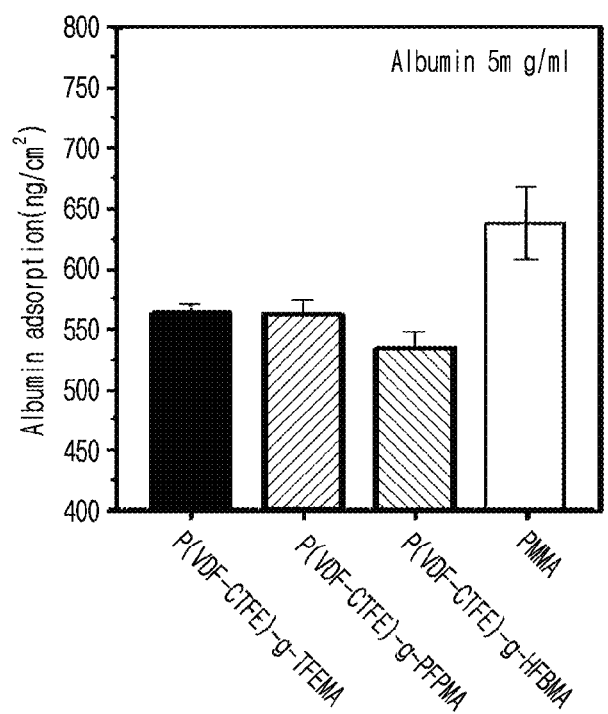
FIG. 2 is a graph showing the albumin adsorption amount of a thin films prepared in each of Example 4 to Example 6 and Comparative Example 1.

FIG. 2 is a chart showing the measurement of the adsorption of a hydrophobic thin film with respect to a single model protein albumin (P(VDF-CTFE)-g-TFEMA:Example 4, P(VDF-CTFE)-g-PFPMA:Example 5, P(VDF-CTFE)-g-HFBMA:Example 6, PMMA:Comparative Example 1).

As shown in FIG. 2, it can be seen that in the case of albumin, an adsorption amount decreases as hydrophobicity increases.

Figure 3:
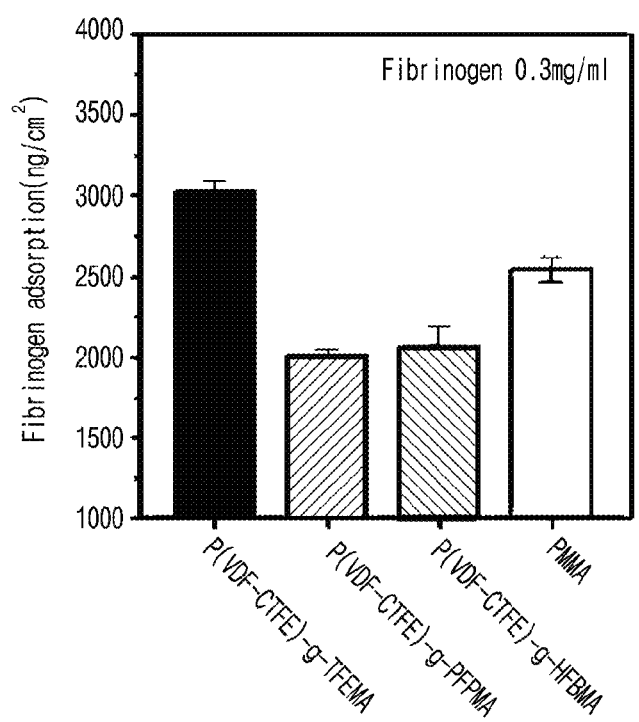
FIG. 3 is a graph showing the fibrinogen adsorption amount of a thin film prepared in each of Example 4 to Example 6 and Comparative Example 1.
Figure 4:
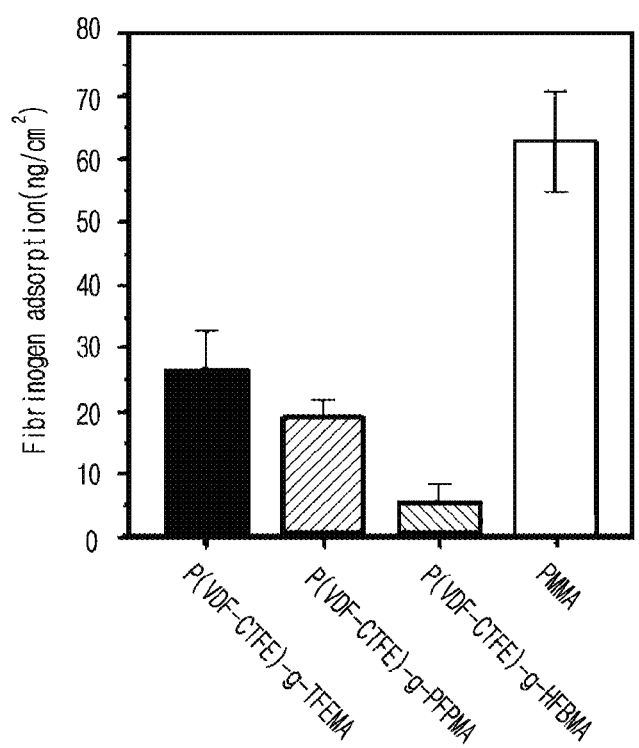
FIG. 4 is a graph showing the fibrinogen adsorption amount of a thin film prepared in each of Example 4 to Example 6 and Comparative Example 1 after the surface of albumin is coated.

FIG. 3 is a chart showing the measurement of the adsorption of a hydrophobic thin film with respect to fibrinogen, which is a protein that inhibits single model protein blood compatibility, and it can be seen that lower adsorption amounts are exhibited in Examples 5 and 6 in which hydrophobicity is high.

FIG. 4 shows results of continuously measuring the adsorption amount of fibrinogen after a hydrophobic film is coated with albumin.

As shown in FIG. 4, the adsorption amount of fibrinogen significantly decreased after the coating of albumin, and it can be seen that the degree of decrease in the adsorption amount is larger as a thin film has higher hydrophobicity.

<Experimental Example 3> Mechanism Analysis of Hydrophobic Thin Film

A fluorine polymer proposed in the present invention has maximized hydrophobicity, so that the surface of a hydrophobic thin film containing the same may form a strong bond due to an induced interaction with protein, and when albumin (known not to be involved in blood clotting), which is a kind of protein contained in blood, is coated on the surface of a hydrophobic thin film formed of the fluorine polymer of the present invention, the albumin is uniformly coated thereon with a strong bond. A comparison of the mechanism is shown in FIG. 6.

Figure 6:
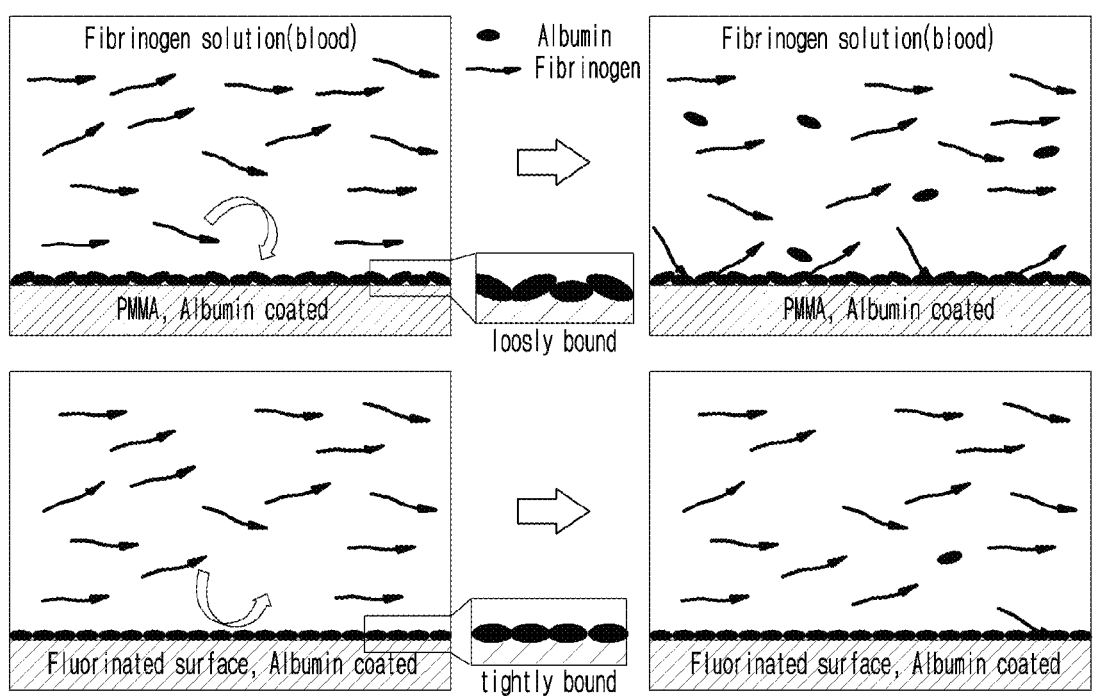
FIG. 6 is a schematic view describing various mechanisms of albumin-fibrinogen replacement on the surface of a hydrophobic thin film formed of a fluorine polymer proposed in one aspect of the present invention and on the surface of a PMMA thin film.

As the mechanism shown in FIG. 6, compared to a PMMA thin film, a hydrophobic thin film formed of the fluorine polymer proposed in the present invention forms a strong bond with albumin, so that uniform coating is achieved on the surface of the film, and in the case of the PMMA thin film, albumin is periodically released, so that the possibility of the attachment of fibrinogen (a protein involved in blood clotting), which is the main cause of inhibiting blood compatibility in blood, increases.

On the other hand, in the case of a hydrophobic thin film formed of the fluorine polymer proposed in the present invention, coated albumin is strongly bonded to the surface of the hydrophobic thin film, and thus, is not separated, so that it is possible to observe low adsorption of fibrinogen, which does not happen on a hydrophobic surface, may be observed.

<Experimental Example 4> Analysis of Platelet Adsorption Experiment

The adsorption of platelets of a hydrophobic thin film according to the present invention and a PMMA thin film was confirmed. Using a scanning electron microscope, the surface of each of bare P(VDF-CTFE)-g-HFBMA, albumin-treated (PVDF-CTFE)-g-HFBMA, bare PMMA, and albumin-treated PMMA was observed, and the number of platelets on the surface was calculated, and is shown in FIG. 7.

As shown in FIG. 7, when comparing the hydrophobic thin film according to the present invention with the PMMA thin film, it can be confirmed that the adsorption of platelets is observed on both thin films. However, after albumin was coated by being adsorbed on a surface (PMMA_alb and -g-HFBMA_alb), it can be confirmed that no adsorption of platelets was observed on the hydrophobic thin film made of the fluorine polymer proposed in the present invention, whereas some platelets were adsorbed on the PMMA thin film. As describe above, it can be confirmed that the adsorption and activity of platelets were significantly reduced.

From the above, it can be seen that hydrophobic thin films prepared through the present invention have better blood compatibility than that of Comparative Example 1 even though they have hydrophobicity.

In addition, for most equipment such as cardiopulmonary bypass equipment or an in vitro oxidizer, a filling solution containing albumin is first flowed to achieve an equilibrate with the inside of a body before using the equipment, which is a similar process to the experiment in FIG. 4.

Therefore, it can be seen that a hydrophobic thin film according to the present invention has excellent blood compatibility, and Example 6 in particular which has the highest hydrophobicity shows an adsorption amount less than 10 nanograms per square centimeter, and thus, has a high possibility of being used as a blood-compatible material.

The invention claimed is:

1. A blood-compatible polymer which is grafted copolymer of vinylidene fluoride (VDF) and chorotrifluoroethylene (CTFE) grafted only with monomer of fluorine-based methacrylate, wherein the fluorine-based methacrylate is represented by the below formula A:

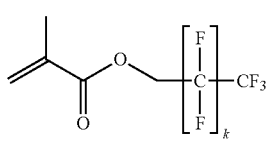

A wherein k is an integer of 0 to 6,
and wherein the blood-compatible polymer is represented by Formula 1 below:

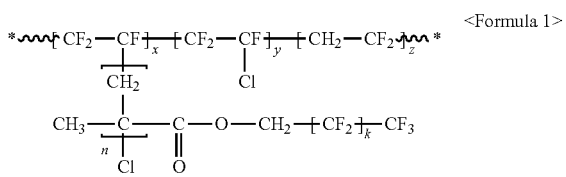

<Formula 1> in Formula 1 above, x is a mole fraction and is a real number satisfying $0<x<1$, y is a mole fraction and is a real number satisfying $0<y<1$, z is a mole fraction and is a real number satisfying $0<z<1$, wherein $x+y+z=1$, n is an integer of 5 to 200, and k is an integer of 0 to 6.

2. A method for preparing a blood-compatible polymer of claim 1, the method comprising mixing a metal catalyst, a ligand, a solvent, and a fluorinated methacrylate monomer by using a copolymer (P(VDF-CTFE)) of vinylidene fluoride (VDF) and chlorotrifluoroethylene (CTFE) as a macro initiator to prepare a mixed solution.

3. The method according to claim 2, wherein the fluorinated methacrylate monomer is one or more selected from the group consisting of trifluoroethyl methacrylate (TFEMA), pentafluoropropyl methacrylate (PFPMA), heptafluorobutyl methacrylate (HFBMA), and nonafluorohexyl methacrylate.

4. A blood-compatible polymer composition comprising a blood-compatible polymer of claim 1 and a solvent.

5. The blood-compatible polymer composition according to claim 1, wherein the composition is applied to a device selected from the group consisting of a blood container, in vitro blood circulation equipment, and body transplant medical equipment.

6. A method for preparing a hydrophobic thin film, the method comprising:
dissolving the polymer of claim 1 in a solvent to prepare a mixed solution; and
coating the mixed solution.

7. The method according to claim 6, wherein the solvent is one or more selected from the group consisting of trifluorotoluene, acetone, ethylmethylketone, tetrahydrofuran, dimethylformamide, chloroform, and N-methyl-2-pyrrolidone (NMP).

8. The method according to claim 6, wherein the coating is performed by one or more methods selected from the group consisting of spin coating, dip coating, roll coating, solution coating, and spray coating.

9. A freestanding polymer film comprising the blood-compatible polymer of claim 1.

10. The freestanding polymer film according to claim 9, wherein the polymer film is applied to a device selected from the group consisting of a blood container, in vitro blood circulation equipment, and body transplant medical equipment.

* * * * *